(12) United States Patent
Hughes et al.

(10) Patent No.: US 8,716,521 B2
(45) Date of Patent: May 6, 2014

(54) FORMULATIONS OF CANFOSFAMIDE AND THEIR PREPARATION

(75) Inventors: Betsy R. Hughes, Mountain View, CA (US); Robert Steven Lopez, Truckee, CA (US)

(73) Assignee: Telik, Inc., Palo Alto, CA (US)

( * ) Notice: Subject to any disclaimer, the term of this patent is extended or adjusted under 35 U.S.C. 154(b) by 39 days.

(21) Appl. No.: 13/619,774

(22) Filed: Sep. 14, 2012

(65) Prior Publication Data

US 2013/0217653 A1    Aug. 22, 2013

Related U.S. Application Data

(60) Division of application No. 13/035,637, filed on Feb. 25, 2011, now Pat. No. 8,324,426, which is a continuation-in-part of application No. 12/511,245, filed on Jul. 29, 2009, now abandoned.

(60) Provisional application No. 61/092,580, filed on Aug. 28, 2008.

(51) Int. Cl.
*C07C 229/00*    (2006.01)

(52) U.S. Cl.
USPC .......................................................... 562/448

(58) Field of Classification Search
None
See application file for complete search history.

(56) References Cited

U.S. PATENT DOCUMENTS

2006/0135409 A1 *   6/2006   Boulanger et al. ................ 514/7

* cited by examiner

*Primary Examiner* — Rosalynd Keys
*Assistant Examiner* — Jennifer C Sawyer
(74) *Attorney, Agent, or Firm* — Foley & Lardner LLP

(57) ABSTRACT

This invention provides stable, lyophilized formulations of canfosfamide as well as the methods of preparation of those stable lyophilized formulations.

11 Claims, 1 Drawing Sheet

FORMULATIONS OF CANFOSFAMIDE AND THEIR PREPARATION

I. CROSS-REFERENCE TO RELATED APPLICATION

This application is a divisional of U.S. patent application Ser. No. 13/035,637 filed on 25 Feb. 2011, now U.S. Pat. No. 8,324,426, which is a continuation-in-part of U.S. application Ser. No. 12/511,245, filed on 29 Jul. 2009 now abandoned, which claims the priority under 35 U.S.C. 119(e) of U.S. Provisional Application No. 61/092,580, filed 28 Aug. 2008, the entire disclosure of all of which is incorporated herein by reference.

II. BACKGROUND OF THE INVENTION

A. Field of the Invention

This invention relates to stable lyophilized formulations of canfosfamide and their preparation.

B. Description of the Related Art

McIntyre and Castañer, "Canfosfamide Hydrochloride", Drugs Fut., 29(10), 985-991 (2004), describe canfosfamide hydrochloride (USAN), a phosphorodiamidate anticancer agent activated by glutathione S-transferase P1-1. The article also identifies canfosfamide hydrochloride with the codes TER-286 and TLK-286.

Morgan et al., "Tumor Efficacy and Bone Marrow-sparing Properties of TER286, a Cytotoxin Activated by Glutathione S-Transferase", Cancer Research, 58(12), 2568-2575 (1998) describe preclinical studies on canfosfamide hydrochloride, including animal studies. According to the article, "for some studies, it was prepared in 60 mM sodium citrate for i.v. delivery."

Tew et al., "TLK-286: a novel glutathione S-transferase-activated prodrug", Expert Opin. Investig. Drugs, 14(8), 1047-1054 (2005), note that "The formulation of TLK-286 in vials containing 265 mg of the sterile lyophilized drug permits solubilization in water for injection to a concentration of 50 mg/ml, followed by dilution to the appropriate dose in 5% dextrose for injection."

The disclosures of the documents referred to in this application are incorporated into this application by reference.

Canfosfamide is a very reactive alkylating agent. Given its reactivity, stable formulations of this compounds have been difficult to develop. Aqueous solutions form only in a narrow range of pH in which the drug is soluble. However, such aqueous formulations are stable for perhaps 6 to 12 hours before decomposition products are observed. Moreover, the reactivity of canfosfamide has made it difficult to find formulation excipients which are stable with the drug.

III. SUMMARY OF THE INVENTION

This invention is directed to the surprising discovery that otherwise unstable aqueous formulations of cansfosfamide or its salt can be lyophilized and maintained as a stable formulation for exceptionally long periods of time rendering the lyophilized formulation suitable for therapeutic utility. One of the most commonly used salts of canfosfamide is the hydrochloride salt which is exemplified here. However, this invention also provides the formulations using other acid salts of canfosfamide such as canfosfamide hydrobromide and the like.

Accordingly, in one embodiment, this invention provides a stable lyophilized formulation consisting essentially of canfosfamide hydrochloride and sodium citrate, wherein the said formulation is stable for therapeutic utility. Preferably, the composition has an osmolality of no more than 400 mM. In another preferred embodiment, the stable lyophilized formulation is prepared without the addition of any lyophilization aids.

In another embodiment, this invention provides a stable lyophilized formulation consisting of canfosfamide hydrochloride and sodium citrate, wherein the said formulation is stable for therapeutic utility, and the said formulation is a product of lyophilization of (50±5) mg/mL canfosfamide hydrochloride and (100±10) mM aqueous sodium citrate buffer at a pH of 4.6±0.2.

In another embodiment, this invention provides a method of preparing a stable lyophilized formulation consisting essentially of canfosfamide hydrochloride and sodium citrate, wherein the said formulation is stable for therapeutic utility, wherein the method comprises:

(a) preparing a sodium citrate buffer of a pH of 6.5±0.1;
(b) dissolving canfosfamide hydrochloride in the sodium citrate buffer of step (a) to provide a solution;
(c) adjusting the pH of the solution of step (b) when pH is >4.8 to provide a resulting solution of pH of 4.6±0.2 by addition of a compatible acid selected from citric acid and HCl; and
(d) lyophilizing the resulting solution of step (c) to provide the said formulation.

IV. DETAILED DESCRIPTION OF THE INVENTION

A. DEFINITIONS

"Consisting of" is a term of limitation and it excludes any element, step, or ingredient not specified in the claim. "Consisting essentially of" is a term of limitation and means to include the presence of stated components, groups, steps, and the like and to exclude the presence of others that materially alter the basic characteristics of what is being claimed or described. Thus a formulation consisting essentially of canfosfamide hydrochloride contains canfosfamide hydrochloride and not another active ingredient or another salt of canfosfamide except for incidental impurities. "Comprising" is a term of inclusion and not of limitation and means to include the presence of stated components, groups, steps, and the like but not to exclude the presence or addition of other components, groups, steps, and the like. Unless the context clearly requires otherwise, the singular includes the plural; so that, for example, "a sodium salt of citric acid" includes both a single such salt and two or more such salts.

A "sodium citrate buffer" is a solution consisting essentially of a sodium salt of citric acid, and optionally citric acid, dissolved in water, typically at a stated pH. The amount of citric acid depends, of course, on the pH of the aqueous solution. Thus, when used herein, the term "sodium citrate buffer" is meant to contain both sodium citrate and citric acid.

A "lyophilized formulation" refers to a formulation resulted from freeze-drying of an aqueous solution.

A "lyophilization aid" refers to one or more additives that help in assisting the lyophilization process. "Lyophilization aids" as per this invention include any one of the following: lubricants, anhydrous lactose, matrix forming agents, and the like.

A "reconstituted formulation" refers to a formulation resulted from adding water (for example, sterile water) or an aqueous solvent to a solid composition in an amount to dissolve the composition. In one embodiment, the solid composition is a lyophilized formulation.

An "injectable formulation" refers to a formulation that is suitable for parenteral administration, e.g., subcutaneous, intravenous, intramuscular, or intraperitoneal administration.

A formulation "stable for therapeutic utility" refers to canfosfamide formulation that over a period of at least 6 months and preferably at least 2 years does not contain more than 2 weight % vinyl sulfone as a decomposition product.

Because the formulation of this invention contains salts dissolved in water, it will necessarily contain dissociated ions as well as non-ionized species. Accordingly, describing the formulation as consisting essentially of canfosfamide hydrochloride in sodium citrate buffer does not describe the association of canfosfamide with hydrochloric acid, or a particular state of ionization of the canfosfamide (which has an amine and two carboxylate groups), or the association of sodium ions with citrate/hydrogen citrate/dihydrogen citrate ions, or other associations or ionization states, but rather that the formulation contains the product of the dissolution of the stated ingredients at the stated concentration in water at the stated pH.

B. BRIEF DESCRIPTION OF THE DRAWINGS

C. THE CANFOSFAMIDE FORMULATION

Figure 1:
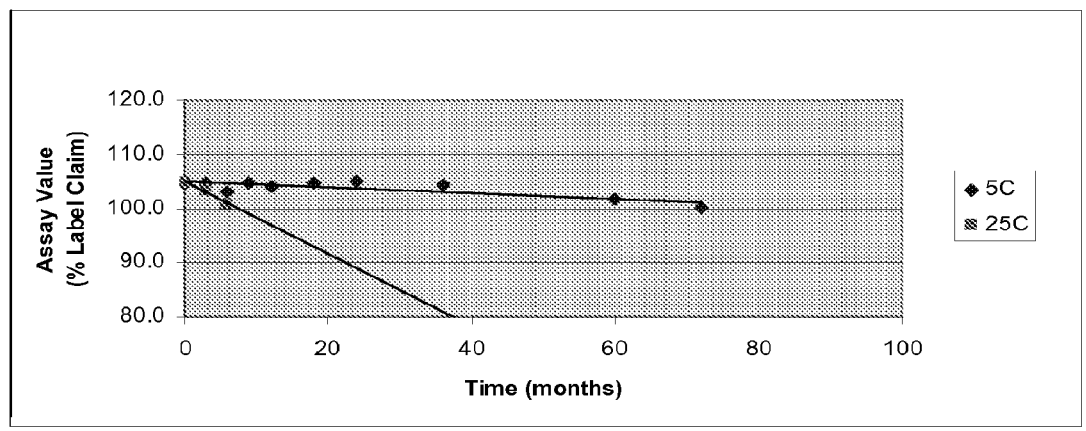
FIG. 1 illustrates a plot of assay value of lyophilized canfosfamide hydrochloride formulation versus time.

A targeted approach to the treatment of solid tumors involves the development of potent alkylating agents activated by glutathione S-transferase P1-1 (GST P1-1). The novel nitrogen mustard prodrug canfosfamide, commonly used as its hydrochloride salt, is one such compound that is useful as a powerful antitumor agent in the treatment of cancer. However, canfosfamide has a limited shelf-life at room temperature as it degenerates quickly to form vinyl sulfone as a major degradation product. Nonetheless, canfosfamide needs to be administered at high doses, for example, at 960 mg/m$^2$ or about 1.5 grams in a single administration, for the treatment of cancer. Thus, there is a need for a stable formulation having a high canfosfamide concentration for intravenous administration and a convenient method for the attending clinician to prepare such a stable formulation when needed.

In one embodiment, this invention provides stable lyophilized formulations and convenient methods that allow preparation of these formulations suitable for intravenous administration to a patient in a needed amount at the time canfosfamide is to be administered.

a. Aqueous Solubility

It has been discovered that aqueous solubility of canfosfamide hydrochloride is strongly dependent on the pH of the solvents. It is poorly soluble in water at about 2 mg/mL and is more soluble at high pH and strengths of the buffers. Canfosfamide hydrochloride is soluble at pH above 4.2 and it has limited stability at pH above pH 5.0. The compounding of the drug product and final pH is therefore in a narrow range. Due to the acidic nature of canfosfamide hydrochloride, its dissolution into a pH 6.5 buffered solution reduces the pH. A buffer system which could keep the final solution pH between 4.3 and 5.0 is therefore essential for the dissolution and for the stability of the in process bulk solution used for formulating the product. Different buffer systems (citrate, succinate, histidine acetate, phosphate) were studied and citrate buffer system showed highest solubility. For example, the solubility of canfosfamide hydrochloride can be as high as 174 mg/mL in 0.2 M pH 5.5 citrate buffer. Thus the aqueous solubility of canfosfamide hydrochloride is dependent on the pH and strengths of the buffers.

Due to the presence of two carboxylic acid groups and one equivalent of hydrochloric acid, canfosfamide hydrochloride has high acidity and dissolution of canfosfamide hydrochloride lowers the pH of the solution significantly even in the presence of a buffer system. For example, when canfosfamide hydrochloride is dissolved into a 0.1 M (100 mM) pH 6.5 citrate buffer, the pH can be reduced to below 5. Once the solution pH is reduced to below pH 4.2, the solubility of canfosfamide hydrochloride is dramatically reduced and drug oils out.

However, canfosfamide is unstable in alkaline environment. High pH buffer or even high local pH of the aqueous solvent leads to degradation of canfosfamide. Thus, back titrating of canfosfamide hydrochloride with a low pH solution would result in significant degradation of canfosfamide hydrochloride. For example, when a 50 mg/mL canfosfamide hydrochloride in a pH 4.3 citrate buffer was titrated with a 0.1 N and a 1.0 N NaOH solution to pH 4.5, the content of a degradation product, vinyl sulfone, was increased from 0.64% to 1.3% and 6.5% from 0.1 N and 1.0 N NaOH titrated solutions respectively. Based on the discovery that canfosfamide hydrochloride is soluble at pH above 4.2 and such aqueous formulations have sufficient stability at a pH below 5, albeit limited to less than that required for a suitable shelf-life, a buffer system which could keep the pH of the final solution at between 4.3 to 5.0 is therefore essential for the dissolution and for the stability of the bulk solution used for formulating lyophilized canfosfamide hydrochloride. Thus, a high concentration of buffer system which can provide a high buffering capacity is desired.

The solubility of canfosfamide hydrochloride depends on the concentration and initial pH of buffer system. Higher buffer concentration and higher initial pH dissolves greater amounts of canfosfamide hydrochloride. A 0.1 M citrate buffer at pH 6.5 could dissolve approximately 100 mg/mL canfosfamide hydrochloride. When 50 mg/mL canfosfamide hydrochloride is dissolved in this buffer system, the pH is about 4.6. The solution has an osmolality of about 400 mM. A higher strength citrate buffer could dissolve more canfosfamide hydrochloride, but it also results in higher osmolality which could make freeze drying challenging and decrease the stability of a lyophilized product. A high osmolality buffer at pH 4.6 could also cause infusion irritation.

Accordingly, there are numerous and divergent constraints on the formation of a lyophilized canfosfamide hydrochloride formulation and each of these constraints must be met in order to provide for a pharmaceutically acceptable formulation.

b. Formulation Critical Parameters

The following items are some critical issues for the compounding of the drug product.

If the solution pH is higher than target pH, it can be titrated with 1.0 NHCL to the target pH. If the pH is too low, it will not be possible to back titrate with NaOH due to the sensibility of canfosfamide hydrochloride to alkaline environment.

Due to the acidity of the drug substance, the rate of dissolution of drug substance influences the pH of the compounding solution. A quick dissolution could reduce the pH faster and therefore reduce the time of exposure of the drug to high pH. A study of 50 mL batch size showed that dissolution at 5° C. was slower than at room temperature (45 minutes versus 25 minutes). The solution was then analyzed by HPLC. The vinyl sulfone generated at 5° C. and room temperature was not significantly different.

An additional study of two liter batch size was conducted. Canfosfamide hydrochloride was dissolved into three batches of pH 6.5, 0.1 M citrate buffer and monitored at different temperatures; 5° C., 20° C. and 40° C. After 80 minutes, the first batch at 5° C., minor particles were observed. In the second batch at 20° C. (room temperature), the drug was totally dissolved after 20 minutes. The amount of vinyl sulfone generated at 5° C. and room temperature was not significantly different. The third batch consisted of adding drug at room temperature and allowing the temperature to increase to 40° C. over 90 minutes. The vinyl sulfone was higher than the two previous batches. These experiments support controlling the compounding procedure at room temperature until all drug is dissolved and filtered.

Canfosfamide hydrochloride is very hydrophilic. It forms lumps with a hydrate layer once in contact with the citrate buffer. This layer prevents further penetration of water into the lumps and slows down the dissolution process. A vigorous agitation using a homogenizer minimizes the lump formation and shortens the mixing time.

The formulation comprising (50±5) mg/mL canfosfamide hydrochloride in (100±10) mM aqueous sodium citrate buffer at pH 4.6±0.2 remained relatively stable with total impurities increased to about 2% after 6 months at 5° C. At 25° C. and 40° C., however, the total impurities increased by 20% and 70% respectively after three months.

Due to the instability of canfosfamide hydrochloride in aqueous solution for an adequate shelf-life, lyophilization of the aqueous formulation was considered. While a higher concentration, high strength citrate buffer could dissolve more canfosfamide hydrochloride, it will also result in a higher osmolality which could make freeze drying challenging and decrease the stability of a lyophilized product. A 50 mg/mL solution of canfosfamide hydrochloride in a 100 mM citrate buffer has an osmolality of about 400 mM, which is close to the limit in performing satisfactory lyophilization to obtain acceptable product. Further, a high osmolality buffer at pH 4.6 could also cause infusion irritation when administered to a patient.

Thus, this invention provides a delicate formulation that achieves high concentration, high stability of canfosfamide and minimizes osmolality by using a 100 nM citrate buffer with an initial pH of about 6.5.

In one embodiment, this invention provides a stable lyophilized formulation consisting essentially of canfosfamide hydrochloride and sodium citrate, wherein the said formulation is stable for therapeutic utility. In a preferred embodiment, the composition has an osmolality of less than 400 mM which permits its therapeutic use for intravenous injection.

Further to minimize osmolality, it is preferred that no bulk agent is added to the formulation. In this regard, it is surprising that canfosfamide hydrochloride (5% w/w) and citrate buffer (3% w/w) act as adequate bulking agents for the lyophilized product. The citrate buffer not only acts as a bulking agent but long term stability tests on the lyophilized product indicates that it has a preservative effect as well. For example, table 1 shows the stability of the formulation:

TABLE 1

Stability of Aqueous versus lyophilized formulation at different temperatures

| Composition | Stability at 5° C. | Stability at room temperature (25° C.) |
|---|---|---|
| Aqueous formulation | 6 months | 7 days |
| Lyophilized product | At least 6 years | About 6 months |

When compared to the aqueous formulation, the lyophilized product when stored at 5° C. has adequate stability of more than 6 years. We believe that the significant increase in stability is unrelated to reaction kinetics because the temperature differential would not support such a vast difference. Hence, we believe that the citrate is acting as a preservative. It was a surprising and unexpected result that the lyophilized formulation would have such a superior stability (>12 times) as compared to the aqueous formulation, particularly as the lyophilized product preferably does not include any lyophilization aids. In some embodiments, no other additives (e.g., anti-oxidants, stabilizers, or chelating agents) are needed.

In another embodiment, this invention provides a stable lyophilized formulation consisting essentially of canfosfamide hydrochloride and sodium citrate, wherein the said formulation is stable for therapeutic utility and has a osmolality of less than 400 mM. Preferably, the lyophilized product does not comprise a lyophilization aid.

In a further embodiment, the stable lyophilized formulation is anhydrous. In another embodiment, the stable lyophilized formulation is stored in a dry atmosphere. In a further embodiment, the dry atmosphere is nitrogen, argon, and the like. In another embodiment, the stable lyophilized formulation is stored at a temperature not higher than 8° C.

c. Stability of Lyophilized Formulation

The lyophilized formulation is generally stable at 5° C. with no significant potency, individual impurities or total impurities change over period having adequate shelf-life (for example, about 18 months). Indeed, the data show that when stored at 5° C., the lyophilized product has a stability for over at least 6 years. Critically, other properties of the lyophilized product such as, appearance, moisture content, pH and reconstitution time were not changed. At 25° C., the lyophilized formulation was found to be stable for about six months. At 25° C., the potency of the lyophilized formulation appears to be reduced over period of 18 months and the total impurities increased. The main impurity that increased was vinyl sulfone.

In another embodiment, this invention provides a stable lyophilized formulation consisting of canfosfamide hydrochloride and sodium citrate, wherein the said formulation has an osmolality of less than 400 mM, is stable for therapeutic utility, and the said formulation is a product of lyophilization of (50±5) mg/mL canfosfamide hydrochloride and (100±10) mM aqueous sodium citrate buffer at a pH of 4.6±0.2. In a further embodiment, the stable lyophilized formulation is stored in a dry atmosphere at a temperature not higher than 8° C.

In another embodiment, this invention provides a stable lyophilized formulation, wherein the said formulation is a product of lyophilization of 50 mg/mL canfosfamide hydrochloride, 100 mM sodium citrate dihydrate, and 2.9 mM citric acid monohydrate in water at a pH of 4.6±0.2, wherein the stable lyophilized formulation is stored in a dry atmosphere at a temperature not higher than 8° C.

In another embodiment, this invention provides a lyophilized formulation of canfosfamide hydrochloride, citric acid and sodium citrate, which formulation is capable of being reconstituted to a formulation consisting essentially of (50±5) mg/mL canfosfamide hydrochloride, (100±10) mM sodium citrate and water, and having a pH of 4.6±0.2.

d. Stability of Bulk Solution

The stable lyophilized formulation of this invention is preferably administered via an injection. Following studies were conducted to check the stability of the bulk solution.

Stability in Solution at 1 mg/mL—Effect of pH

A stability study was performed by monitoring vinyl sulfone generation. Canfosfamide hydrochloride was dissolved at 1 mg/mL into 0.1 M citrated buffer from pH 4.5 to pH 6.5. The solutions were incubated at 25° C. for 24 hours. Vinyl sulfone generation was monitored. Table 2 shows the results of the study.

TABLE 2

Area Percent Vinyl Sulfone at Different pH

| | Percent vinyl sulfone at 25° C. | | |
|---|---|---|---|
| pH | 0 hrs | 6 hrs | 24 hrs |
| 4.5 | ND | 0.1 | 0.4 |
| 5.0 | ND | 0.2 | 1.1 |
| 5.5 | ND | 0.6 | 2.9 |
| 6.0 | ND | 1.7 | 8.2 |
| 6.5 | ND | 6.6 | 24.2 |

ND = not detected

The results show that the stability of canfosfamide hydrochloride is pH dependant. Higher pH generates more vinyl sulfone. However, the amount of vinyl sulfone produced at 25° C. at pH between 4.5 and 5.5 over at least a 6 hour period is sufficiently low such that administration of an intravenous formulation is permitted.

Stability in Solution of Current Formulation (50 mg/mL)

The stability of the bulk solution of 50 mg/mL (at pH 4.6) was conducted. The results showed that at 25° C., the purity was relatively unchanged after 1 day. Table 3 shows the bulk solution stability results.

TABLE 3

Area Percent Canfosfamide Hydrochloride
Upon Bulk Solution Stability (data is ± 2%)

| Time | % Purity 25° C. |
|---|---|
| Day 0 | 92 |
| Day 1 | 89 |
| Day 3 | 93 |
| Day 7 | 89 |
| Day 28 | 84 |
| 3 Month | 69 |
| 6 Month | NP* |

NP: Not performed

The results show that the stability of canfosfamide hydrochloride solution decreases over time at 25° C. However, percent purity decrease at 25° C. is such that immediate (within 24 hours) lyophilization is permitted.

Figure 2:
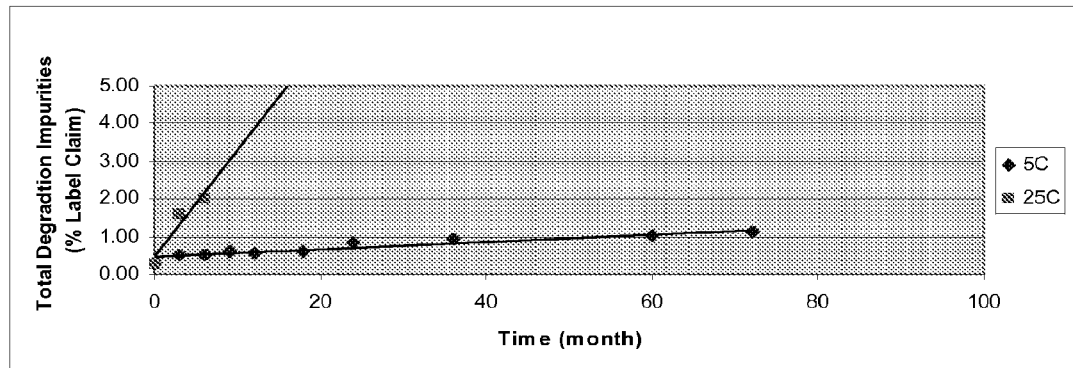
FIG. 2 illustrates a plot of percent total degradation impurities in lyophilized canfosfamide hydrochloride formulation versus time.

FIG. 1, a plot of assay value of lyophilized canfosfamide hydrochloride formulation (50 mg/mL) versus time, illustrates that canfosfamide formulation is stable at 5° C. even after 72 months as seen by the almost unchanged assay value. Similarly, FIG. 2, a plot of total degradation impurities percent versus time, illustrates that the amount of impurities in lyophilized canfosfamide hydrochloride formulation (50 mg/mL) are about 1% even after 72 months.

In another embodiment, this invention provides a kit for preparing an aqueous formulation consisting essentially of (50±5) mg/mL canfosfamide hydrochloride, and (100±10) mM aqueous sodium citrate having a pH of 4.6±0.2, which kit comprises sterile water and a lyophilized formulation comprising canfosfamide hydrochloride, citric acid and sodium citrate capable of being reconstituted to said formulation.

In another embodiment, the kit is for preparing a formulation consisting essentially of (50±5) mg/mL canfosfamide hydrochloride, and (100±10) mM aqueous sodium citrate having a pH of 4.6±0.2, which kit comprises sterile water and a lyophilized formulation of canfosfamide hydrochloride, citric acid and sodium citrate capable of being reconstituted to said formulation.

In another embodiment, this invention provides a reconstituted formulation of canfosfamide hydrochloride, which formulation comprises (50±5) mg/mL canfosfamide hydrochloride in (100±10) mM aqueous sodium citrate buffer at pH 4.6±0.2.

In another embodiment, the reconstituted formulation of canfosfamide consists essentially of (50±5) mg/mL canfosfamide hydrochloride in (100±10) mM aqueous sodium citrate buffer at pH 4.6±0.2.

In some embodiments, the reconstituted formulation is prepared by a process comprising adding water (e.g., sterile water) to the stable lyophilized composition of this invention.

In another embodiment, this invention provides an injectable formulation of canfosfamide comprising (50±5) mg/mL canfosfamide hydrochloride in (100±10) mM aqueous sodium citrate buffer at pH 4.6±0.2, and a diluent so that the final canfosfamide hydrochloride in the injectable formulation is about 6-8 mg/mL canfosfamide hydrochloride.

In some embodiments, this invention provides an injectable formulation of canfosfamide consisting essentially of (50±5) mg/mL canfosfamide hydrochloride in (100±10) mM aqueous sodium citrate buffer at pH 4.6±0.2, and a diluent so that the final canfosfamide hydrochloride in the injectable formulation is about 6-8 mg/mL canfosfamide hydrochloride.

In some embodiments, the diluent is 5% dextrose aqueous solution.

In some embodiments, the injectable formulation is for intravenous administration.

Methods

In another embodiment, this invention is a method of preparing the stable lyophilized formulations consisting essentially of canfosfamide hydrochloride and sodium citrate, wherein the said formulation is stable for therapeutic utility, wherein the method comprises:

(a) preparing a sodium citrate buffer of a pH of 6.5±0.1;
(b) dissolving canfosfamide hydrochloride in the sodium citrate buffer of step (a) to provide a solution;
(c) adjusting the pH of the solution of step (b) when pH is >4.8 to provide a resulting solution of pH of 4.6±0.2 by addition of a compatible acid selected from citric acid and HCl; and
(d) lyophilizing the resulting solution of step (c) to provide a lyophilized formulation having an osmolality of less than 400 mM.

In a further embodiment, the method does not comprise addition of a lyophilization aid.

In another embodiment, the method further comprises storing the lyophilized formulation of step (d) in a dry atmosphere at a temperature not higher than 8° C. In a further embodiment, the dry atmosphere is nitrogen or argon.

The aqueous sodium citrate buffer may be prepared by the dissolution of a predetermined amount of one or more sodium citrate salts, and optionally citric acid, for example trisodium citrate dihydrate and citric acid monohydrate, in water, followed if necessary by an adjustment of the pH to the desired value of 6.5±0.1 by the addition of an acid, such as hydrochloric acid, or a base, such as 1 M sodium hydroxide.

In some embodiments, the pH 6.5 of the 0.1 M citrate buffer is achieved by titrating sodium citrate solution with citric acid to obtain pH 6.5.

In some embodiments, the pH 6.5, 0.1 M citrate buffer is prepared by dissolving a predetermined amount of sodium citrate and a predetermined amount of citric acid, followed if necessary by an adjustment of the pH to the desired value of 6.5±0.1 by the addition of an acid.

The canfosfamide hydrochloride is added to the buffer and stirred to achieve dissolution. The addition of the canfosfamide hydrochloride to the buffer will reduce the pH of the mixture to approximately 4.6±0.2, or slightly higher; and the pH of the mixture may be reduced by the addition of small quantities of acid if it exceeds 4.8. Addition of the canfosfamide hydrochloride to the aqueous citrate buffered solution is preferably conducted at room temperature or below.

Typically, steps (a) through (c) are performed with the use of less water than is required to achieve the desired final concentrations of (50±5) mg/mL canfosfamide hydrochloride and (100±10) mM sodium citrate, and as a final step (c') water is added to achieve the desired final concentrations and an osmolality of less than 400. For example, when the aqueous sodium citrate buffer is prepared by adding solid sodium citrate and then citric acid to water, the initial amount of water in which the buffer ingredients are to be dissolved may be (85-95)% of the amount of water needed to achieve the final concentration, allowing for the use of additional water to rinse in the solid ingredients as the formulation is prepared; then, following any necessary pH adjustment, the remaining amount of water is added to achieve the desired final concentrations.

The resulting formulation may be filtered, such as by filtration through a 0.45 μm filter; and is then typically sterile filtered, such as by filtration through a 0.2 μm filter, and the formulation would then be suitable for injection.

In an embodiment, the formulation steps can be performed under dry conditions, for example, under nitrogen purge.

Then, the formulation is lyophilized for storage (and subsequent reconstitution before administration), using methods conventional in the art with the exception that lyophilization aids are preferably not employed. Lyophilization as per this invention is illustrated in the following Example. For example, the formulation is dispensed into containers of appropriate size, such as 10 mL or 20 mL, frozen in the containers to substantially below 0° C. Removal of the water content of the formulation is achieved under reduced pressure by sublimation. Upon drying, the pressure and temperature are increased, and the containers are sealed to provide for the lyophilized composition.

The quantity per container of the formulation will typically be chosen to permit reconstitution to the same concentration as the original formulation and withdrawal of a convenient amount (e.g. 250 mg or 1 g) of canfosfamide hydrochloride. For example, 5.3 mL of the formulation (a 6% overage) may be lyophilized in a 10 mL vial, allowing for convenient withdrawal of 5.0 mL of formulation after reconstitution with 5.2 mL water to provide 250 mg of canfosfamide hydrochloride; 10.3 mL of the formulation of this invention may be lyophilized in 20 mL vial to provide 515 mg of canfosfamide hydrochloride, and 20.6 mL of the formulation (a 3% overage) may be lyophilized in a 50 mL vial, allowing for convenient withdrawal of 20.0 mL of the formulation after reconstitution to provide 1.0 g of canfosfamide hydrochloride.

EXAMPLES

The following example describes the lyophilized formulations of this invention, and their preparation. The mixing and filtration operation were conducted under nitrogen purge.

Example 1

To prepare a 50 L volume of the formulation (density 1.034 Kg/L), 43.5 Kg of water for injection (WFI) was added to a jacketed 80 L stainless steel vessel equipped with a Silverson mixer with a 10 cm stainless steel blade. This was stirred at 800 r.p.m.; 1470 g trisodium citrate dihydrate was added and rinsed in with 1 L of WFI; and stirring was continued for 10 minutes. Citric acid monohydrate, 30.2 g, was added and rinsed in with 500 mL of WFI; and stirring was continued at 1320 r.p.m. for a further 10 minutes. The pH of the solution was measured and adjusted to 6.6 by the addition of two 20 mL increments of 1 M hydrochloric acid, with 5 minutes of stirring at 1320 r.p.m. after each addition. Canfosfamide hydrochloride, 2600 g of 96.8% pure material, was added and rinsed in with 1500 mL of WFI; and stirring was continued for 20 minutes at 2300 r.p.m. and 30 minutes at 2200 r.p.m. The pH of the solution was measured as 4.7. A further 1 Kg of WFI was added and stirred for 10 minutes at 880 r.p.m., after which the solution was cooled to 8° C., giving 50 L of the formulation of this invention, containing 50.3 mg/mL of canfosfamide hydrochloride in 103 mM sodium citrate buffer at pH 4.7.

The formulation was filtered through a 0.45 μm filter and then through two 0.2 μm filters (sterile filtration). The filtered formulation was filled into 10 mL type I glass vials with 5.3 mL fill volume per vial; a 20 mm butyl rubber lyophilization stopper was placed in the lyophilization position on each vial; and the vials were placed onto trays and loaded into the lyophilizer, with the lyophilizer shelves at 5° C. Once the lyophilizer was closed, the lyophilization cycle comprised: hold for 0.6 hours; decrease shelf temperature to −46° C. over 1.7 hours; hold for 5 hours; decrease lyophilizer chamber pressure to 13.3 Pa over 0.8 hours; start nitrogen gas sweep at 12.4 Pa and hold for 5 hours; increase shelf temperature to −25° C. over 1.1 hours; hold for 16.2 hours; increase shelf temperature to 0° C. over 1 hour; hold for 20 hours; increase shelf temperature to 30° C. over 1.7 hours; hold for 15 hours; decrease shelf temperature to 8° C. over 0.6 hours; increase lyophilizer chamber pressure to 69 KPa with nitrogen; stopper the vials; increase lyophilizer chamber pressure to atmospheric pressure; open the lyophilizer and unload the stoppered vials. Each vial contained a lyophilized formulation of this invention containing 265 mg canfosfamide hydrochloride and 159 mg trisodium citrate/citric acid. The vials were sealed with an aluminum seal with a flip-off polypropylene cap. When reconstituted with 5.2 mL of WFI, each vial contains 5.3 mL of an aqueous formulation containing 50.3 mg/mL of canfosfamide hydrochloride in 103 mM sodium citrate buffer at pH 4.7; allowing convenient withdrawal of 5.0 mL of the formulation.

An aqueous formulation containing 50 mg/mL of canfosfamide hydrochloride may also be lyophilized in vials of other sizes if a larger unit dose is required, such as 20 mL vials with a fill volume of 10.3 mL, 50 mL vials with a fill volume of 20.6 mL, giving a canfosfamide hydrochloride content of 1030 mg (1 g plus 3% overage per vial). The lyophilization cycle may require modification (e.g. lengthening of the cycle time) for larger fill volumes, but such modification will be within the capability of a person of ordinary skill in the art having regard to that skill and this disclosure.

For intravenous (i.v.) injection, the reconstituted formulation with 50 mg/mL canfosfamide was diluted 7 times (1 part to 6 part) with a 250 mL 5% Dextrose Injection solution in an i.v. bag to form an i.v. injectable formulation. Both the reconstituted formulation and the i.v. injectable formulation were stable at room temperature for 24 hours.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claimed:

1. A method of preparing a stable lyophilized formulation consisting essentially of canfosfamide hydrochloride and sodium citrate, wherein the said formulation is stable for therapeutic utility for at least 18 months at 5° C. and has a pH of 4.6±0.2 when reconstituted with water, which method comprises:
    (a) preparing a sodium citrate buffer of a pH of 6.5±0.1;
    (b) dissolving canfosfamide hydrochloride in the sodium citrate buffer of step (a) to provide a solution;
    (c) adjusting the pH of the solution of step (b) when pH is >4.8 to provide a resulting solution of pH of 4.6±0.2 by addition of a compatible acid; and
    (d) lyophilizing the resulting solution of step (c) to provide the said formulation.

2. The method of claim 1, wherein the said formulation does not contain a lyophilization aid and has an osmolality of less than 400 mM when reconstituted to an aqueous composition comprising (50±5) mg/mL canfosfamide hydrochloride.

3. The method of claim 1, wherein the said formulation is anhydrous.

4. The method of claim 1, wherein the said formulation is stored in a dry atmosphere.

5. The method of claim 4, wherein the dry atmosphere is nitrogen or argon.

6. The method of claim 1, wherein the said formulation is stored at a temperature not higher than 8° C.

7. The method of claim 1, wherein the method does not comprise addition of a lyophilization aid.

8. The method of claim 1, wherein the method further comprises storing the lyophilized formulation of step (d) in a dry atmosphere at a temperature not higher than 8° C.

9. The method of claim 8, wherein the dry atmosphere is nitrogen.

10. The method of claim 8, wherein the dry atmosphere is argon.

11. The method of claim 1, wherein the compatible acid is selected from citric acid and hydrochloric acid.

* * * * *